(12) United States Patent
Panin

(10) Patent No.: US 11,234,958 B2
(45) Date of Patent: Feb. 1, 2022

(54) FORMULATION BASED ON VITAMIN E OR AN ESTER THEREOF FOR TREATING BACTERIAL AND FUNGAL BIOFILMS

(71) Applicant: BIO.LO.GA. S.R.L., Conegliano (IT)

(72) Inventor: Giorgio Panin, Rovigo (IT)

(73) Assignee: BIO.LO.GA S.R.L., Conegliano (IT)

( * ) Notice: Subject to any disclaimer, the term of this patent is extended or adjusted under 35 U.S.C. 154(b) by 124 days.

(21) Appl. No.: 16/683,684

(22) Filed: Nov. 14, 2019

(65) Prior Publication Data

US 2020/0121638 A1    Apr. 23, 2020

Related U.S. Application Data

(63) Continuation-in-part of application No. PCT/EP2018/063926, filed on May 28, 2018.

(30) Foreign Application Priority Data

May 29, 2017   (IT) .................. 102017000058311

(51) Int. Cl.

| | |
|---|---|
| *A61K 31/355* | (2006.01) |
| *A61P 31/04* | (2006.01) |
| *A61P 31/02* | (2006.01) |
| *A61P 31/10* | (2006.01) |
| *A61K 9/00* | (2006.01) |
| *A61K 9/06* | (2006.01) |
| *A61K 47/34* | (2017.01) |

(52) U.S. Cl.
CPC .......... *A61K 31/355* (2013.01); *A61K 9/0014* (2013.01); *A61K 9/06* (2013.01); *A61K 47/34* (2013.01); *A61P 31/02* (2018.01); *A61P 31/04* (2018.01); *A61P 31/10* (2018.01)

(58) Field of Classification Search
CPC .... A61K 31/355; A61K 47/34; A61K 9/0014; A61K 9/06; A61K 47/14; A61K 47/24; A61P 31/04; A61P 31/02; A61P 31/10
USPC .......................................................... 514/458
See application file for complete search history.

(56) References Cited

U.S. PATENT DOCUMENTS

| | | | |
|---|---|---|---|
| 3,755,558 | A | 8/1973 | Scribner et al. |
| 6,280,752 | B1 | 8/2001 | Panin |
| 2020/0360339 | A1* | 11/2020 | Panin ................... A61K 31/355 |

FOREIGN PATENT DOCUMENTS

| | | | |
|---|---|---|---|
| JP | H09169643 | * | 6/1997 |
| JP | H09169643 A | | 6/1997 |
| WO | 2010121081 A1 | | 10/2010 |

(Continued)

OTHER PUBLICATIONS

Davide Campoccia, et al., "Baterial Adhesion to Poly-(D,L)Lactic Acid Blended With Vitamin E: Toward Gentle Anti-Infective Biomaterials", Journal of Biomedical Materials Research, Part A, vol. 103, No. 4, pp. 1447-1458, 2014.

(Continued)

*Primary Examiner* — Taylor V Oh
(74) *Attorney, Agent, or Firm* — Lucas & Mercanti, LLP

(57) ABSTRACT

Formulations for topical use based on vitamin E or an ester thereof for use in removing, reducing or inhibiting a bacterial and/or fungal biofilm, are disclosed. The ester of vitamin E is an ester with a carboxylic acid of formula R—COOH, in which R is an alkyl radical having from 1 to 19 carbon atoms, or an alkenyl or alkynyl having from 2 to 19 carbon atoms.

17 Claims, 3 Drawing Sheets

(56) References Cited

FOREIGN PATENT DOCUMENTS

WO 2017050668 A1 3/2017
WO 2017119009 A1 7/2017

OTHER PUBLICATIONS

Sumitkumar Jagani, et al., Effects of Phenol and Natural Phenolic Compounds on Biofilm Formation by Pseudomonas Aeruginosa, Biofouling: The Journal of Bioadhesion and Biofilm Research, vol. 25, No. 4, pp. 321-324, 2009.

Ashlynn L.Z. Lee, et al., "Block Copolymer Mixtures as Antimicrobial Hydrogels for Biofilm Eradication", Biomaterials, vol. 34, No. 38, p. 10278-10286, 2013.

F. D. Matl, et al., "New Anti-Infective Coatings of Medical Implants", vol. 52, No. 6, pp. 1957-1963, 2008.

International Search Report and Written Opinion for International Application No. PCT/EP2018/063926 (15 Pages) (dated Jul. 19, 2018).

International Preliminary Report on Patentability for International Application No. PCT/EP2018/063926 (15 Pages) (dated May 9, 2019).

* cited by examiner

FORMULATION BASED ON VITAMIN E OR AN ESTER THEREOF FOR TREATING BACTERIAL AND FUNGAL BIOFILMS

CROSS-REFERENCE TO RELATED APPLICATIONS

This application is a continuation-in-part of PCT International Application Serial No. PCT/EP2018/063926 filed May 28, 2018 which, in turn, claims the benefit of priority from Italian Patent Application Serial No. 102017000058311 filed May 29, 2017, the contents of each of which are incorporated herein by reference.

FIELD OF APPLICATION

The present invention refers to the technical field of the pharmaceutical industry.

In particular, the invention refers to a formulation for topical application for the treatment of a biofilm of pathogenic bacteria or fungi.

BACKGROUND OF THE INVENTION

It is known that a biofilm is a complex aggregation of microorganisms characterized by the secretion of an adhesive and protective extracellular matrix, defined EPS (extracellular polymeric substances).

Said matrix is not a static structure, since it is subjected to considerable variations depending on the type of microorganism that produces it and the growing conditions, although it is possible to identify the recurring presence of some polysaccharides, proteins and nucleic acids, and it represents a high percentage, varying from 50% to 90%, of the organic component of the biofilm, so much to be considered the primary element of this structure.

The biofilm can be present in any natural and artificial environment and is characterized by a noteworthy ability to adhere to surfaces, to guarantee complex interactions among the microbial communities contained therein and, further, to protect them from the action of external agents, including antibiotics.

Indeed, biofilm synthesis represents to date one of the most frequent complications of human infections, to the point of being object of numerous studies at international level.

The severity of such infections lies in the difficulty of diagnosis, in the difficulty of treating and eradicating the microbial community, as well as in the difficulty of prevention.

Indeed, the resistance of this particular microbial community, often of the bacterial type, is considerable and the infections that result therefrom can sometimes cause death. It is estimated that about 65% of human infections are currently related to the production of this extracellular matrix, in which the microorganisms reside and communicate with each other, being able to survive in even extreme environmental conditions.

The treatment of the biofilm-related infections is particularly difficult since the bacteria in this growth mode are intrinsically resistant to antimicrobial drugs and host defences.

A reduced diffusion of drugs through the extracellular matrix, the low growth rate of the cells, the increased ability to exchange genetic elements due to the proximity of the cells, the presence of subpopulations of dormant cells are all factors which are believed to contribute to the resistance of the biofilms to antibiotic treatment.

As a result, any biofilm prevention or disintegration strategy is useful to prevent infections, reducing hospitalizations and hospital costs.

Dhall S et al., (J Diabetes Res, 2014:562625) describe a treatment of injuries in a db/db mouse model having impaired healing by means of administration of alpha-tocopherol and N-acetyl cysteine. After the above-mentioned treatment, it was noted that the biofilm had an increased sensitivity to antibiotics and granulation tissue was formed with proper collagen deposition and remodelling. However, alpha-tocopherol was administered intraperitoneally and only N-acetylcysteine was applied topically.

Lee A L et al., (Biomaterials, 2013 December; 34(38): 10278-86) describe biodegradable hydrogels based on polycarbonates functionalized with vitamin E moiety for antimicrobial application. These hydrogels showed antimicrobial/antifungal effects and the ability to reduce microbe viability of the biofilms.

Campoccia D et al., (J Biomed Res A, 2015 April; 103(4):1447-58) describe the possibility to use polylactic acid (PLA) polymers blended with vitamin E or vitamin E acetate as gentle anti-infective biomaterials. An in vitro experiment with biofilm-producing staphylococci proved a significant decrease in bacterial adhesion and in biofilm accumulation on the surface of these vitamin E (acetate)-enriched polymers.

Jagani S et al. (Biofouling, 2009; 25(4):321-4) evaluated, by microtiter-plate assay, the anti-biofouling activity of 14 phenols and natural phenolic compounds against *Pseudomonas aeruginosa* and it was shown that such compounds, except ethyl linoleate and tocopherol, cause a significant reduction in biofilm formation by *Pseudomonas aeruginosa*.

The technical problem underlying the present invention was that of providing a formulation for topical application that is able to reduce or remove pathogenic bacterial and/or fungal biofilms or to inhibit their formation, and that is suitable for application also on sensitive, intolerant or allergy-prone skin.

SUMMARY OF THE INVENTION

The present invention solves the above-mentioned problem by providing a formulation for topical use based on vitamin E or an ester thereof for use in removing, reducing or inhibiting a bacterial and/or fungal biofilm.

The formulations described herein can be in included in methods of topically treating conditions associated with bacterial and/or fungal biofilm-related infections and/or treating wounds, such as burn wounds, skin ulcers and sores. The methods include topically administering an effective amount of a formulation described herein to an area of the skin in need thereof.

Effective amounts will be understood by those of ordinary skill to be based upon the amount of vitamin E or an ester thereof comprised in the formulation said amount of a vitamin E or an ester thereof being sufficient to obtain a clinical response after one or more topical administrations of the formulations described herein to an affected area of the skin daily.

In one embodiment of the invention where the formulations consist of vitamin E or an ester thereof, the formulations are topically administered in amounts of from about 0.1 to about 10 g/10 cm$^2$ of skin daily. Alternatively, amounts of from about 0.5 to about 2.5 g/10 cm$^2$ of skin, or amounts of from about 0.8 to about 1.2 g/10 cm² of skin or about 1 g/10 cm² of skin is applied topically to the affected area daily.

In an alternative embodiment where the formulations include from about 20 to about 70% of vitamin E acetate and from about 20 to about 70% of a volatile silicone, the methods include topically administering the formulation to the affected area in amounts of from about 0.15 to about 20 g/10 cm² daily with amounts of from about 0.7 g to about 10 g, or from about 1.0 g to about 7 g, or from about 1.5 g to about 5 g, or from about 3 g to about 4 g/10 cm² daily. In this aspect of the invention, it can be seen for example that in the case of Example 2 below, the formulation contains 30% vitamin E acetate, which means that when 3 to 4 g of the formulation are applied, an amount of 0.9 g to 1.2 g of vitamin E is applied and thus about 1 g/10 cm² of skin.

Administration of the formulations of the invention can continue for 7 days in many embodiments with the duration of administration being as long or as short as clinically desirable. In some alternative aspects of this embodiment, the methods of treatment further include irrigation of the affected area with a saline or physiologically acceptable solution prior to the application of the formulations described herein.

Preferably, the ester of vitamin E is an ester with a carboxylic acid of formula R—COOH, in which R is an alkyl radical having from 1 to 19 carbon atoms, or an alkenyl or alkynyl having from 2 to 19 carbon atoms.

Preferably, the ester is alpha-tocopheryl acetate, n-propionate or linoleate.

Preferably, the ester is alpha-tocopheryl acetate.

In an embodiment, the formulation according to the present invention consists of vitamin E or an ester thereof.

Preferably, the formulation consists of vitamin E acetate.

In another aspect, the formulation consists of alpha-tocopheryl acetate.

According to another embodiment, the formulation of the invention comprises, in weight percentage on the total weight of the formulation, 20 to 70% of vitamin E acetate and 20 to 70% of a volatile silicone.

The volatile silicone can be selected from the group comprising pentamer cyclomethicone, tetramer cyclomethicone, hexamer cyclomethicone, hexamethyldisiloxane, low viscosity dimethicone and mixtures thereof.

Preferably, the volatile silicone is a low viscosity dimethicone, such as for example one or more of the dimethicones Belsil DM2 and Belsil DM5 of the firm Wacker or the dimethicones KF-96A-5cs and KF-96A-2cs of the firm Shin Etsu.

Preferably, the formulation further comprises 7 to 13% of hydrogenated castor oil.

Preferably, the formulation further comprises 7 to 15% of an oily component chosen from the group comprising vegetable oils and esters of fatty acids such as octyl palmitate, isopropyl myristate, ethyl oleate and mixtures thereof.

Preferably, the formulation further comprises 2 to 3% of dimethiconol.

In a further embodiment, the formulation according to the present invention comprises in weight percentage on the total weight of the formulation:
from 20 to 65% of vitamin E acetate,
from 20 to 60% of a vegetable butter or a wax,
from 10 to 30% of a triglyceride of caprylic and capric acid,
from 3 to 20% of a gelling agent for lipids selected from triglyceride of palmitic and stearic acid and sorbitan olivate.

Preferably, the formulation further comprises one or more among hydrogenated castor oil, phytosterols, and ceramide.

Preferably, the vegetable butter is shea butter, and the ceramide is ceramide-NP.

By the expression "for topical use" it is hereby meant the use of the formulation by topical application onto a body part, in particular skin, mucosae, hair, nails.

The Applicant has surprisingly found that the formulation for topical application according to the present invention, based on vitamin E or an ester thereof, is able to effectively reduce formation of pathogenic bacterial and/or fungal biofilms, as shown in the Examples.

In an aspect of the present invention, the formulation according to the invention does not contain excipients nor additives and is therefore suitable for topical application also on sensitive, intolerant or allergy-prone skin.

The term "biofilm" identifies a community of microbial, bacterial or fungal nature, characterized by cells which adhere to a biotic or abiotic substrate immersed in a self-produced extracellular polymeric matrix which protects them from the external environment.

DETAILED DESCRIPTION

Figure 1:
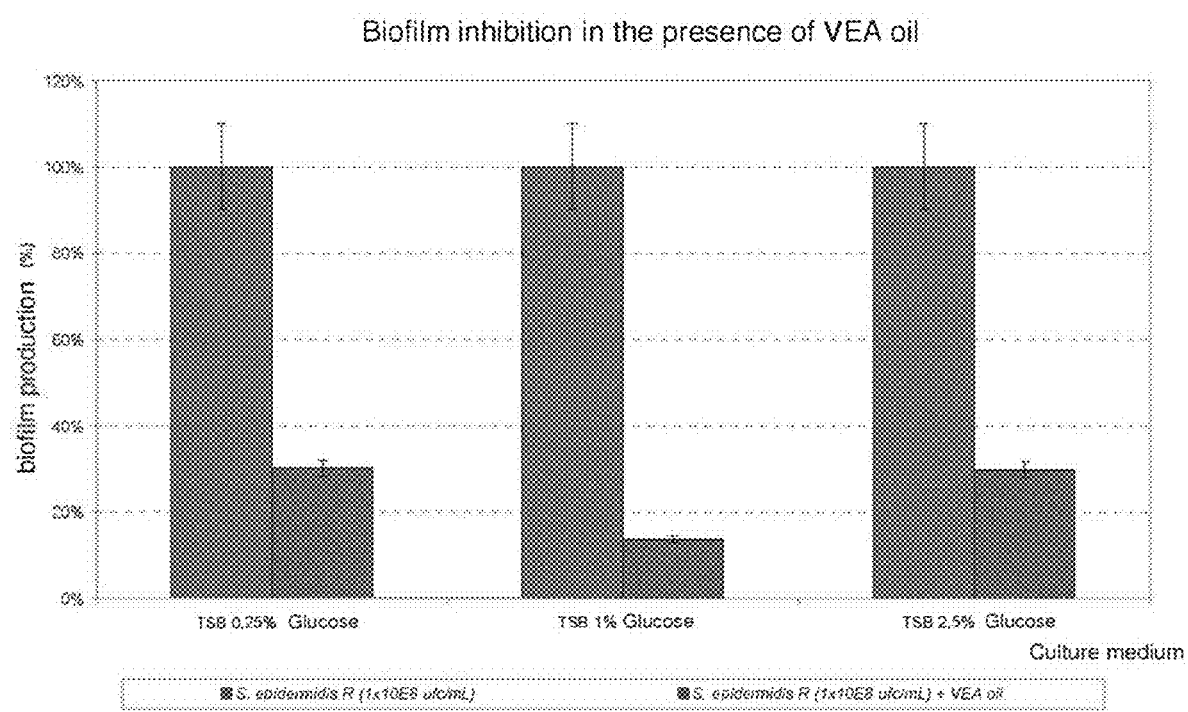
FIG. 1 shows a bar graph of the biofilm production of the strain *Staphylococcus epidermidis* R on TSB medium with variable glucose concentration, with and without the formulation of Example 1 according to the invention.

The present invention will be further described with reference to some non-limiting examples and referring also to the accompanying drawings.

Example 1

An example of formulation that can be used for removing, reducing or inhibiting a bacterial and/or fungal biofilm is the product VEA® Olio, marketed by the firm Hulka S.r.l. from Rovigo and consisting of alpha-tocopheryl acetate.

Example 2

A formulation according to the invention in the form of a hydrophobic gel was prepared according to the following composition, wherein the percentages are by weight on the total composition weight.

| | |
|---|---|
| Pentamer cyclomethicone 245 | 39.5% |
| Vitamin E acetate | 30.0% |
| Hydrogenated castor oil | 10.5% |
| Octyl palmitate | 10.0% |
| 8:2 Cyclomethicone/dimethiconol | 10.0% |

Such formulation was made according to the following procedure.

525 g of hydrogenated castor oil (Cutina HR) and 500 g of octyl palmitate were introduced into a steel-turbine mixer (manufactured by Dumec), and the content was stirred while being heated at about 80-90° temperature until the hydrogenated castor oil dissolved.

Then, 1500 g of vitamin E acetate were added under stirring at the above temperature, and the vacuum was produced inside the mixer (vacuum equal to 600 cm Hg).

Once the desired degree of vacuum had been achieved, 500 g of a pre-formed mixture of 8:2 pentamer cyclomethicone/dimethiconol and 1975 g of pentamer cyclomethicone 245 were added under stirring.

The homogeneous mixture thus obtained was brought to ambient temperature under continuous stirring so as to obtain, in the end, a translucent hydrophobic gel of semi-solid consistence.

100 small plastic jars containing 50 g each were filled with the gel prepared in this way and said jars were properly closed and subjected to a conservation test at different temperatures: −20° C., 3° C. and 30° C. for 90 days, and 60° C. for 21 days.

The aspect of the cream remained unchanged during the entire period of conservation at the above four temperatures, as well as its viscosity and the other rheological characteristics.

Example 3

Another formulation according to the invention in the form of a hydrophobic gel was prepared according to the following composition, wherein the percentages are by weight on the total composition weight.
tocopheryl acetate: 30%
shea butter: 24%
triglyceride of caprylic and capric acid: 21.7%
sorbitan olivate: 14%
phytosterols: 10%
ceramide-NP: 0.3%

The method of preparation is as follows: a first phase comprising Vitamin E, phytosterols and ceramides is prepared by heating the whole mixture up to 120° C. to obtain a homogeneous solution. The other ingredients are heated up to 60° C. in a separate container. The two phases are then combined together and mixed for about 30 minutes at room temperature.

Example 4

The selection of biofilm-producing strains for performing the in vitro tests described in the following Example 5 was carried out as follows.

At first, the selection envisaged a screening step on 30 strains of microorganisms, using a method to establish the production of biofilm by the assayed strains, which is described below.

The strains were cultured on TSB medium (tryptic soy broth, i.e. a nutritious medium which supports growth of a broad range of microorganisms) which was used for pre-inoculation.

Subsequently, the strains were subjected to the method for quantification of the produced biofilm according to Srdjan Stepanovic et al. (Stepanovic S., Vukovic D., Dakic I., Savic B., Svabic-Vlahovic M., "A modified microtiter-plate test for quantification of staphylococcal biofilm formation", Journal of Microbiological Methods 2000; 40:175-179) and said method is described below.

The tubes containing TSB previously incubated at 37° C. for 24 hours were centrifuged at 3000 rpm for 10 minutes, the supernatant was then removed, and the pellet was resuspended in the following media: TSB with 0.25%, 1% and 2.5% of D-glucose.

A 96-well plate containing 200 µl of bacterial suspension was then prepared and incubated at 37° C. for 24 hours. Once the incubation period was ended, the content of the single wells was aspirated and the wells of the plate were washed 3 times with 250 µl of sterile physiological solution (NaCl 9 g/L) and, at each wash, the plate was turned upside down to remove excess physiological solution.

The cells were then fixed, adding to each well 200 µl of 99% methanol for 15 minutes; then, the wells were emptied and dried.

The 96-well plate was then stained for 5 minutes adding to each well 200 µl of a 2% crystal violet solution, after which the plate was washed with tap water and let to dry.

The dye bound to the adhering cells was re-solubilized with 160 µl of 33% glacial acetic acid (v/v) per well; the plate was read at the microplate reader (Victor) at a wavelength of 570 nm before and after adding the 33% glacial acetic acid.

For the purposes of comparative analysis of the results, a classification in four categories based on the adhesion ability of the tested strains, was introduced.

All strains were classified in the following categories: non adherent (0), weakly (+), moderately (++) or strongly (+++) adherent, depending on the optical density values of bacterial biofilms.

The limit ("cut-off") of the optical density ($OD_c$) for the microtiter-plate was defined as three standard deviations above the mean OD of the negative control.

The strains were classified as follows:
$OD \leq OD_c$—non adherent
$OD_c < OD \leq 2 \times OD_c$—weakly adherent
$2 \times OD_c < OD \leq 4 \times OD_c$—moderately adherent
$4 \times OD_c < OD$—strongly adherent All the tests were performed in triplicates and the average of the results was calculated.

After such screening step was concluded, the microbial strains used for the in vitro tests were *Staphylococcus epidermidis* R (isolated from clinical samples) and *Staphylococcus aureus* (isolated from clinical samples).

Example 5

The Applicant tested the ability to reduce, remove and inhibit biofilm of *Staphylococcus epidermidis* R and *Staphylococcus aureus* of the product VEA® Olio, marketed by the firm Hulka S.r.l., consisting of alpha-tocopheryl acetate 100%.

A 96-well plate was prepared in quadruplicate for each condition envisaged by the experiment, all the tests were performed on TSB with 0.25%, 1% and 2.5% of D-glucose.

The set-out conditions were the following:
1. *Staphylococcus epidermidis* R and *Staphylococcus aureus* (with a count of $1 \times 10^8$ cfu/mL) without adding VEA Olio (positive control);
2. *Staphylococcus epidermidis* R and *Staphylococcus aureus* (with a count of $1 \times 10^8$ cfu/mL) loaded in the well only after uniformly coating the plate well with VEA Olio.

FIG. 1 shows that, on TSB medium with 0.25% of glucose, biofilm production by the strain *Staphylococcus epidermidis* R was 30% with a 70% reduction of the production in the presence of VEA Olio.

In TSB medium with 1% of glucose, the above strain showed a biofilm production of 14% with a reduction of 86% in the presence of VEA Olio, while on TSB medium with 2.5% of glucose it showed a production of 30% with a consequent reduction of 70% in the presence of VEA Olio.

Figure 2:
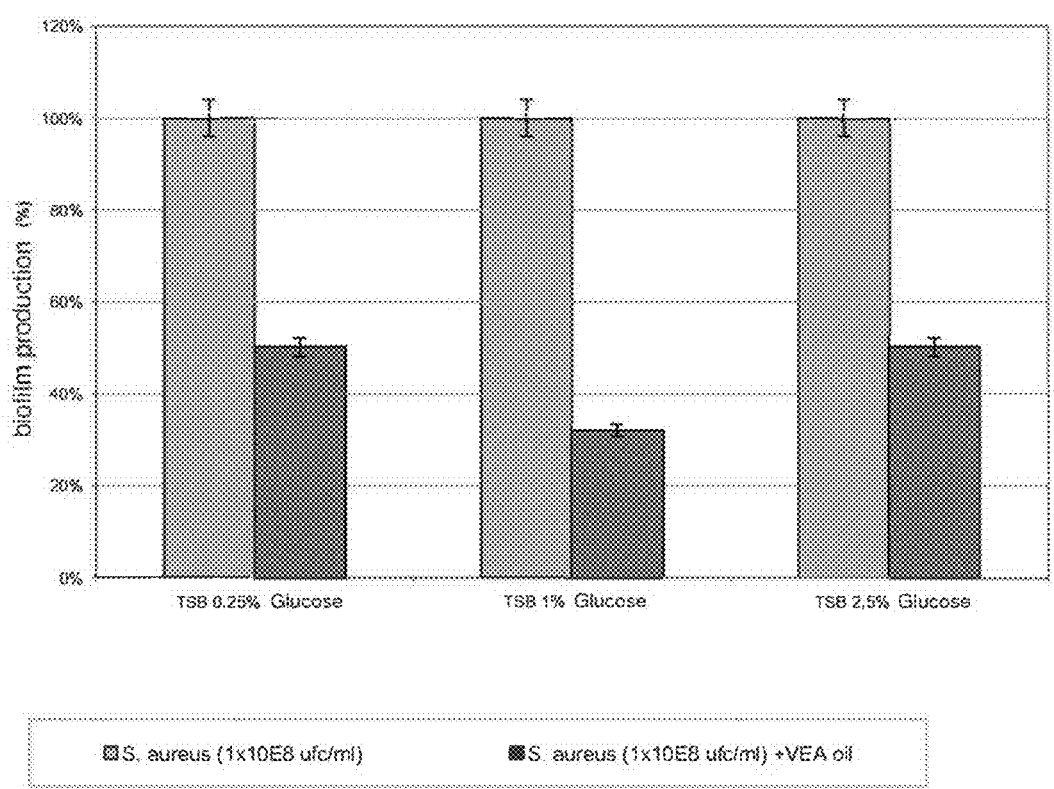
FIG. 2 shows a bar graph of the biofilm production of the strain *Staphylococcus aureus* on TSB medium with variable glucose concentration, with and without the formulation of Example 1 according to the invention.

FIG. 2 shows that, on TSB medium with 0.25% of glucose, the biofilm production by the strain *Staphylococcus aureus* was 50%, with a 50% reduction of the production in the presence of VEA Olio.

In TSB medium with 1% of glucose, the strain at issue showed a biofilm production of 32% with a reduction of 68% in the presence of VEA Olio, while on the TSB medium with 2.5% of glucose it showed a production of 50% with a consequent reduction of 50% in the presence of VEA Olio.

These results show that alpha-tocopheryl acetate used for the experiments plays a surprising inhibitory activity with respect to biofilm formation.

Example 6

VEA® Olio was also tested for the ability to reduce, remove and inhibit biofilm of the following microorganisms: *Staphylococcus aureus* *Staphylococcus epidermidis*, *Escherichia coli*, *Klebsiella pneumoniae*, *Proteus mirabilis*, *Acinetobacter baumannii*, *Pseudomonas aeruginosa* and *Pseudomonas putida* (Table 1).

A 96-well plate was prepared in quadruplicate for each condition envisaged by the experiment, all the tests were performed on TSB with or without VEA® Olio.

TABLE 1

Biofilm production on TBS medium with or without VEA Olio.

| Medium | | Mean OD* | Standard Deviation | Test T | D** | Biofilm production |
|---|---|---|---|---|---|---|
| S. aureus | TSB | 0.33 | 0.04 | 0.07 | 0.26 | 100% |
| ATCC 29213 | TSB + VEA Olio | 0.26 | 0.05 | | 0.11 | 44% |
| S. epidermidis | TSB | 0.53 | 0.07 | 0.03 | 0.45 | 100% |
| [Code R9] | TSB + VEA Olio | 0.33 | 0.13 | | 0.18 | 39% |
| E. coli ATCC | TSB | 0.36 | 0.10 | 0.96 | 0.28 | 100% |
| 11775 | TSB + VEA Olio | 0.35 | 0.15 | | 0.20 | 73% |
| K. pneumonie | TSB | 0.41 | 0.10 | 0.87 | 0.34 | 100% |
| ATCC 700603 | TSB + VEA Olio | 0.40 | 0.06 | | 0.26 | 76% |
| P. mirabilis | TSB | 0.36 | 0.07 | 0.16 | 0.28 | 100% |
| CECT 4168 | TSB + VEA Olio | 0.28 | 0.06 | | 0.14 | 49% |
| A. baumannni | TSB | 0.34 | 0.06 | 0.88 | 0.26 | 100% |
| ATCC 19606 | TSB + VEA Olio | 0.34 | 0.07 | | 0.20 | 76% |
| P. aeruginosa | TSB | 0.33 | 0.08 | 0.25 | 0.25 | 100% |
| ATCC 27853 | TSB + VEA Olio | 0.27 | 0.05 | | 0.12 | 49% |
| P. putida | TSB | 0.45 | 0.09 | 0.03 | 0.38 | 100% |
| | TSB + VEA Olio | 0.30 | 0.07 | | 0.15 | 39% |
| No microorganism inoculated (blank) | TSB | 0.08 | | | | |
| | TSB + VEA Olio | 0.15 | | | | |

*OD is the optical density at 570 nm.
**D is the difference between the mean optical density measured for each microorganism and the optical density of the blanks (TSB and TSB VEA Olio respectively).

Table 1 shows that biofilm production by several types of microorganisms was strongly inhibited on medium TSB+ VEA Olio.

For example, the biofilm production by *P. aeruginosa* was 49%, *S. epidetmidis* was 39% and *S. aureus* was 44%, considering the biofilm production on TSB medium as 100%.

These results show that alpha-tocopheryl acetate used for these experiments displays a surprising inhibitory activity with respect to biofilm formation by different microorganisms.

Example 7

The gel obtained according to Example 2 was tested for the ability to reduce, remove and inhibit biofilm of same microorganisms cited in Example 6 (Table 2).

The experimental conditions were the same of Example 6.

TABLE 2

Biofilm production on TBS medium with or without gel according to Example 2.

| Medium | | Mean OD* | Standard Deviation | Test T | D** | Biofilm production |
|---|---|---|---|---|---|---|
| S. aureus | TSB | 0.35 | 0.11 | 0.0034 | 0.28 | 100% |
| ATCC 29213 | TSB + GEL | 0.69 | 0.10 | | 0.17 | 62% |
| S. epidermidis | TSB | 0.58 | 0.10 | 0.1335 | 0.51 | 100% |
| [Code R9] | TSB + GEL | 0.69 | 0.08 | | 0.16 | 33% |
| E. coli ATCC | TSB | 0.30 | 0.07 | 0.0035 | 0.23 | 100% |
| 11775 | TSB + GEL | 0.64 | 0.13 | | 0.12 | 53% |
| P. mirabilis | TSB | 0.42 | 0.10 | 0.0058 | 0.34 | 100% |
| CECT 4168 | TSB + GEL | 0.66 | 0.07 | | 0.14 | 41% |
| A. baumannni | TSB | 0.37 | 0.09 | 0.0021 | 0.30 | 100% |
| ATCC 19606 | TSB + GEL | 0.68 | 0.08 | | 0.16 | 53% |
| P. aeruginosa | TSB | 0.38 | 0.08 | 0.0273 | 0.31 | 100% |
| ATCC 27853 | TSB + GEL | 0.69 | 0.20 | | 0.17 | 54% |
| P. putida | TSB | 0.35 | 0.08 | 0.0069 | 0.28 | 100% |
| | TSB + GEL | 0.69 | 0.15 | | 0.17 | 60% |
| No microorganism (blank) | TSB | 0.07 | | | | |
| | TSB + GEL | 0.52 | | | | |

*OD is the optical density at 570 nm.
**D is the difference between the mean optical density measured for each microorganism and the optical density of the blanks (TSB and TSB + GEL respectively).

Table 2 shows that biofilm production by several types of microorganism was strongly inhibited on medium TSB+ GEL (according to Example 2).

For example, the biofilm production by *P. aeruginosa* was 54%, *P. mirabilis* was 41% and *S. epidermidis* was 33%, considering the biofilm production on TSB medium as 100%.

Example 8

In this Example, 20 patients with mid-deep and deep burn wounds (average TBSA approximately 42%, range 25-67%) were selected. Patients average age was 47.75 years (ranging 25-72 years), 8 were males. The presence of exudate, pain and delayed re-epithelialization, absence of tissue necrosis and/or sepsis were criteria of topical use of the composition of Example 1, "VEA Olio", avoiding conventional treatments such as local antibiotics, polyurethane foams and other occlusive dressings. Exclusion criteria were the presence of severe renal or hepatic failure, positive history of myocardial infarction, ischemic or haemorrhagic stroke, coagulation or psychological disorders.

After careful removing all epidermal debris and wound irrigation with saline solution, wound tissue cultures were daily obtained and sent to the Microbiological Unit of the Pisa University Hospital, for 10 consecutive days.

In each patient, two clinically similar areas were identified and treated every 24 hours as listed below:

Group 1: topical application of VEA Olio—composition of Example 1;

Group 2: conventional medication (e.g. silver dressings, collagenases, topical antimicrobials).

TABLE 1

Group 1 patients' data and culture samples results.

| | | | | Microbiological cultures | | | | | | | | | | |
|---|---|---|---|---|---|---|---|---|---|---|---|---|---|---|
| No. | Age | Sex | TBSA (%) | Day 0 | Day 1 | Day 2 | Day 3 | Day 4 | Day 5 | Day 6 | Day 7 | Day 8 | Day 9 | Day 10 |
| 1 | 49 | M | 34 | P.a. | P.a. | P.a. | P.a. | P.a. | P.a. | P.a. | — | — | — | — |
| 2 | 67 | F | 46 | C.p. | C.p. | C.p. | C.p. | C.p. | — | — | — | — | — | — |
| 3 | 64 | F | 37 | S.h. | S.h | S.h. | S.h. | — | — | — | — | — | — | — |
| 4 | 53 | F | 29 | S.h. | — | — | — | — | — | — | — | — | — | — |
| 5 | 44 | F | 67 | P.a. | P.a. | P.a. | P.a. | P.a. | — | — | — | — | — | — |
| 6 | 47 | M | 53 | P.a. | P.a. | P.a. | P.a. | P.a. | — | — | — | — | — | — |
| 7 | 49 | F | 48 | C.a. | C.a. | C.a. | C.a. | C.a. | — | — | — | — | — | — |
| 8 | 35 | M | 56 | S.e. | S.e. | S.e. | S.e. | — | — | — | — | — | — | — |
| 9 | 68 | F | 43 | C.p. | C.p. | — | — | — | — | — | — | — | — | — |
| 10 | 51 | F | 28 | P.m. | P.m. | P.m. | P.m. | — | — | — | — | — | — | — |
| 11 | 25 | M | 56 | P.a. | P.a | P.a. | P.a. | P.a | — | — | — | — | — | — |
| 12 | 72 | M | 34 | C.p. | C.p. | C.p. | C.p. | — | — | — | — | — | — | — |
| 13 | 36 | F | 46 | P.a. | P.a. | — | — | — | — | — | — | — | — | — |
| 14 | 60 | M | 25 | C.a. | C.a. | C.a. | C.a. | C.a. | C.a. | — | — | — | — | — |
| 15 | 44 | F | 51 | P.m. | P.m. | P.m. | — | — | — | — | — | — | — | — |
| 16 | 32 | M | 35 | P.a. | P.a. | P.a. | — | — | — | — | — | — | — | — |
| 17 | 58 | F | 47 | C.p. | C.p. | C.p. | C.p. | — | — | — | — | — | — | — |
| 18 | 34 | F | 42 | S.c. | S.c. | S.c. | S.c. | S.c. | — | — | — | — | — | — |
| 19 | 41 | M | 27 | P.a. | P.a. | P.a. | P.a. | — | — | — | — | — | — | — |
| 20 | 26 | F | 38 | C.a. | C.a. | C.a. | — | — | — | — | — | — | — | — |

C.p. *Candida parapsilosis*,
C.a. *Candida albicans*,
P.m. *Proteus mirabilis*,
P.a. *Pseudomonas aeruginosa*,
S.c. *Staphylococcus capitis*,
S.e. *Staphylococcus epidermidis*,
S.h. *Staphylococcus haemolyticus*

TABLE 2

Group 2 patients' data and culture samples results.

| | | | | Microbiological cultures | | | | | | | | | | |
|---|---|---|---|---|---|---|---|---|---|---|---|---|---|---|
| No. | Age | Sex | TBSA (%) | Day 0 | Day 1 | Day 2 | Day 3 | Day 4 | Day 5 | Day 6 | Day 7 | Day 8 | Day 9 | Day 10 |
| 1 | 49 | M | 34 | P.a. | P.a. | P.a. | P.a. | P.a. | P.a. | P.a. | P.a. | P.a. | P.a. | — |
| 2 | 67 | F | 46 | P.m. | P.m. | P.m. | P.m. | P.m. | P.m. | P.m. | P.m. | P.m. | — | — |
| 3 | 64 | F | 37 | S.h. | S.h. | S.h. | S.h. | S.h. | S.h. | S.h. | S.h. | S.h. | — | — |
| 4 | 53 | F | 29 | S.e. | S.e. | S.e. | S.e. | S.c. | S.e. | S.e. | S.e. | — | — | — |
| 5 | 44 | F | 67 | P.a. | P.a. | P.a. | P.a. | P.a. | P.a. | P.a. | P.a. | — | — | — |
| 6 | 47 | M | 53 | P.a. | P.a. | P.a. | P.a. | P.a. | P.a. | P.a. | P.a. | P.a. | P.a. | — |
| 7 | 49 | F | 48 | C.a. | C.a. | C.a. | C.a. | C.a. | C.a. | C.a. | C.a. | C.a. | C.a. | — |
| 8 | 35 | M | 56 | S.c. | S.e. | S.e. | S.e. | S.c. | Se. | S.e. | — | — | — | — |
| 9 | 68 | F | 43 | S.c. | S.c. | S.c. | S.c. | S.c. | S.c. | S.c. | S.c. | — | — | — |
| 10 | 51 | F | 28 | P.m. | P.m. | P.m. | P.m. | P.m. | P.m. | P.m. | P.m. | P.m. | — | — |
| 11 | 25 | M | 56 | P.a. | P.a. | P.a. | P.a. | P.a. | P.a. | P.a. | P.a. | — | — | — |
| 12 | 72 | M | 34 | C.p. | C.p. | C.p. | C.p. | C.p. | — | — | — | — | — | — |
| 13 | 36 | F | 46 | P.a. | P.a. | P.a. | P.a. | P.a. | P.a. | P.a. | P.a. | — | — | — |
| 14 | 60 | M | 25 | C.a. | C.a. | C.a. | C.a. | C.a. | C.a. | C.a. | C.a. | C.a. | — | — |
| 15 | 44 | F | 51 | P.m. | P.m. | P.m. | P.m. | P.m. | P.m. | P.m. | P.m. | — | — | — |
| 16 | 32 | M | 35 | P.a. | P.a. | P.a. | P.a. | P.a. | P.a. | P.a. | — | — | — | — |
| 17 | 58 | F | 47 | C.p. | C.p. | C.p. | C.p. | C.p. | C.p. | C.p. | C.p. | C.p. | C.p. | — |
| 18 | 34 | F | 42 | S.c. | S.c. | S.c. | S.c. | S.c. | S.c. | S.c. | S.c. | — | — | — |

TABLE 2-continued

Group 2 patients' data and culture samples results.

| No. | Age | Sex | TBSA (%) | Day 0 | Day 1 | Day 2 | Day 3 | Day 4 | Day 5 | Day 6 | Day 7 | Day 8 | Day 9 | Day 10 |
|---|---|---|---|---|---|---|---|---|---|---|---|---|---|---|
| 19 | 41 | M | 27 | P.a. | P.a. | P.a. | P.a. | P.a. | P.a. | P.a. | P.a. | P.a. | P.a. | — |
| 20 | 26 | F | 38 | C.a. | C.a. | C.a. | C.a. | C.a. | C.a. | C.a. | C.a. | C.a. | C.a. | — |

C.p. *Candida parapsilosis*,
C.a. *Candida albicans*,
P.m. *Proteus mirabilis*,
P.a. *Pseudomonas aeruginosa*,
S.c. *Staphylococcus capitis*,
S.e. *Staphylococcus epidermidis*,
S.h. *Staphylococcus haemolyticus*.

RESULTS

Figure 3:
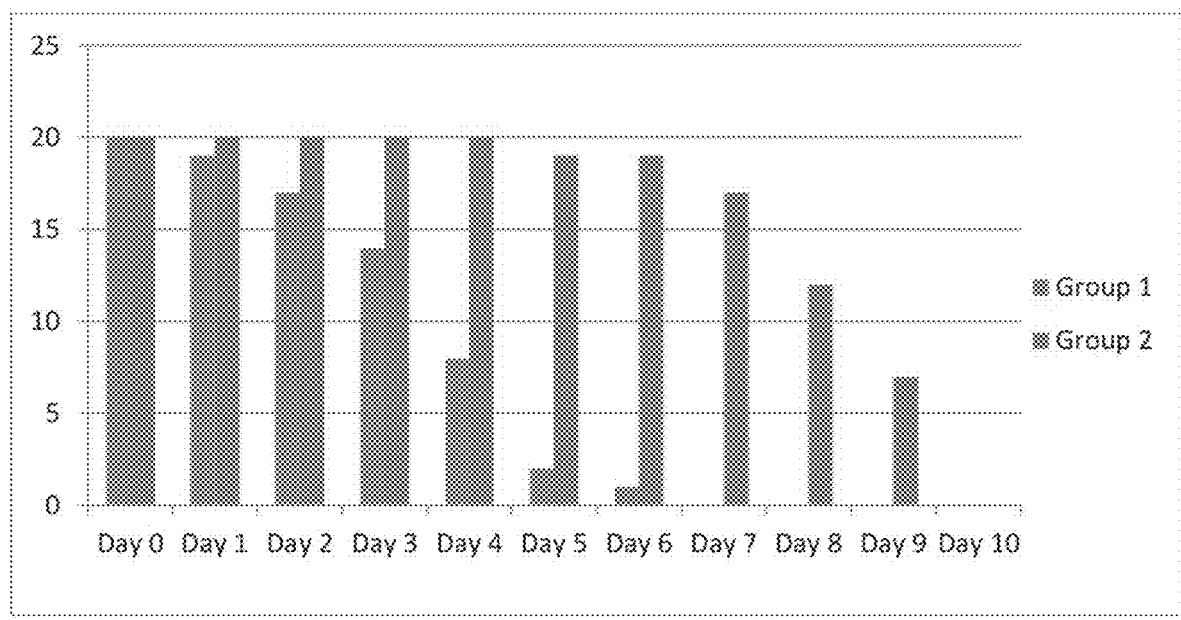
FIG. 3 shows a bar graph displaying the comparative treatment results from Example 8 using the inventive composition and a control.

Patients data and culture samples results are summarized in Tables 1 and 2. All the patients had positive results for bacterial cultures before treatment. The isolated organism cultured from the wound tissue in Group 1 were *Pseudomonas aeruginosa* (N=7, 35%), *Candida parapsilosis* (N=4, 20%), *C. albicans* (N=3, 15%), *Staphylococcus haemolyticus* (N=2, 10%), *Proteus mirabilis* (N=2, 10%), *Staphylococcus epidermidis* (N=1, 5%), *Staphylococcus capitis* (N=1, 5%). Despite the presence of initial bacterial infection, a quicker reduction of exudates and pain and a progressive and faster bacterial load reduction was observed in the Group 1 (See FIG. 3). Clinically several macroscopic changes of granulating tissue were observed. Negative cultures were obtained after average 3 days in Group 1 (range 1-6 days) and 8 days in Group 2 (range 5-9 days).

Referring again to FIG. 3, the number of positive cultures found in the two groups set forth. It can be seen that the number of positive bacterial cultures in the group of patients treated with tocopherol acetate (Group I) decrease much more quickly and becomes 0 at day 7 than in the group of patients treated with conventional medications (Group 2).

This example shows the importance of the therapeutic targeting of infection in the treatment of burns. As the compositions of the invention stimulated granulation tissue, it reduced bacterial growth, modulated angiogenesis and improved epithelialization.

The invention claimed is:

1. A method of removing, reducing or inhibiting a bacterial biofilm on an area of a patient's skin, comprising topically applying a formulation selected from the group consisting of vitamin E and an ester thereof to the area of the skin requiring such treatment.

2. The method of claim 1, wherein said ester of vitamin E is an ester with a carboxylic acid of formula R—COOH, in which R is an alkyl radical having from 1 to 19 carbon atoms, or an alkenyl or alkynyl having from 2 to 19 carbon atoms.

3. The method of claim 2, wherein said ester is alpha-tocopheryl acetate, n-propionate or linoleate.

4. The method of claim 3, wherein said ester is alpha-tocopheryl acetate.

5. The method of claim 1, wherein said formulation consists of vitamin E acetate.

6. The method of claim 1, wherein said formulation consists of alpha-tocopheryl acetate.

7. The method of claim 1, wherein said formulation is applied to the area requiring treatment daily.

8. The method of claim 7, wherein the amount of the formulation applied to the skin daily is from 0.1 to 10 g/10 cm$^2$ of skin.

9. The method of claim 8, wherein the amount of the formulation applied to the skin daily is from 0.5 to 2.5 g/10 cm$^2$ of skin.

10. The method of claim 9, wherein the amount of the formulation applied to the skin daily is from 0.8 to 1.2 g/10 cm$^2$ of skin.

11. A method of removing, reducing or inhibiting a bacterial biofilm on an area of a patient's skin, which comprises topically applying a formulation consisting of in weight percentages on the total weight of the formulation,
   20 to 70% of vitamin E acetate,
   20 to 70% of a volatile silicone,
   7 to 13% of hydrogenated castor oil,
   7 to 15% of an oily component selected from the group consisting of vegetable oils, and esters of fatty acids, said esters of fatty acids being selected from the group consisting of octyl palmitate, isopropyl myristate and ethyl oleate and mixtures thereof, and
   2 to 3% of dimethiconol,
to the area of skin requiring such treatment.

12. The method of claim 11, wherein said volatile silicone is selected from the group consisting of pentamer cyclomethicone, tetramer cyclomethicone, hexamer cyclomethicone, hexamethyldisiloxane, low viscosity dimethicone and mixtures thereof.

13. The method of claim 11, wherein the amount of the formulation applied to the skin daily is from 0.15 to 20 g/10 cm$^2$ of skin.

14. The method of claim 13, wherein the amount of the formulation applied to the skin daily is from 1.0 to 7 g/10 cm$^2$ of skin.

15. The method of claim 14, wherein the amount of the formulation applied to the skin daily is from 1.5 to 5 or from 3 g to 4 g/10 cm$^2$ of skin.

16. A method of removing, reducing or inhibiting a bacterial biofilm on an area of a patient's skin having a burn wound thereon, comprising topically applying a formulation consisting of in weight percentages on the total weight of the formulation,
   20 to 70% of vitamin E acetate,
   20 to 70% of a volatile silicone,
   7 to 13% of hydrogenated castor oil,
   7 to 15% of an oily component selected from the group consisting of vegetable oils, and esters of fatty acids, said esters of fatty acids being selected from the group consisting of octyl palmitate, isopropyl myristate and ethyl oleate and mixtures thereof, and
   2 to 3% of dimethiconol,
to the area of skin requiring such treatment.

17. A method of removing, reducing or inhibiting a bacterial biofilm on an area of a patient's skin having a burn wound thereon, comprising topically applying a formulation selected from the group consisting of vitamin E and an ester thereof to the area of skin requiring such treatment.

* * * * *